US009198860B2

(12) United States Patent
Ishii et al.

(10) Patent No.: US 9,198,860 B2
(45) Date of Patent: Dec. 1, 2015

(54) PARTICULATE PHARMACEUTICAL COMPOSITION

(75) Inventors: Atsushi Ishii, Kashiwa (JP); Yasuki Kato, Kashiwa (JP)

(73) Assignee: NANOCARRIER CO., LTD., Kashiwa-shi (JP)

(*) Notice: Subject to any disclaimer, the term of this patent is extended or adjusted under 35 U.S.C. 154(b) by 512 days.

(21) Appl. No.: 13/122,546

(22) PCT Filed: Feb. 14, 2011

(86) PCT No.: PCT/JP2011/053052

§ 371 (c)(1), (2), (4) Date: Jun. 14, 2011

(87) PCT Pub. No.: WO2011/099601

PCT Pub. Date: Aug. 18, 2011

(65) Prior Publication Data

US 2012/0076866 A1 Mar. 29, 2012

(30) Foreign Application Priority Data

Feb. 12, 2010 (JP) ................................ 2010-029486

(51) Int. Cl.

| | |
|---|---|
| ***A61K 9/14*** | (2006.01) |
| ***A61K 31/7088*** | (2006.01) |
| ***A61K 38/02*** | (2006.01) |
| ***A61K 9/107*** | (2006.01) |
| ***A61K 31/7084*** | (2006.01) |
| ***A61K 9/16*** | (2006.01) |
| ***A61K 9/19*** | (2006.01) |
| ***A61K 47/24*** | (2006.01) |
| ***A61K 47/34*** | (2006.01) |

(52) U.S. Cl.

CPC ................. *A61K 9/1075* (2013.01); *A61K 9/16* (2013.01); *A61K 9/19* (2013.01); *A61K 31/7084* (2013.01); *A61K 47/24* (2013.01); *A61K 47/34* (2013.01)

(58) Field of Classification Search

CPC ..... A61K 47/24; A61K 47/34; A61K 9/1075; A61K 9/19; A61K 31/7084; A61K 9/16

See application file for complete search history.

(56) References Cited

U.S. PATENT DOCUMENTS

| | | | | |
|---|---|---|---|---|
| 5,449,513 | A | 9/1995 | Yokoyama et al. | |
| 5,510,103 | A | 4/1996 | Yokoyama et al. | |
| 7,202,954 | B2 * | 4/2007 | Washizu et al. | 356/451 |
| 2005/0026287 | A1 | 2/2005 | Crouzet et al. | |
| 2006/0134221 | A1 | 6/2006 | Geall | |
| 2008/0311040 | A1 * | 12/2008 | Berry et al. | 424/9.1 |
| 2009/0258079 | A1 | 10/2009 | Katakai et al. | |
| 2009/0291130 | A1 | 11/2009 | Ohuchi et al. | |
| 2011/0268772 | A1 * | 11/2011 | Kim et al. | 424/400 |

FOREIGN PATENT DOCUMENTS

| | | | |
|---|---|---|---|
| CN | 1468095 | | 1/2004 |
| CN | 101489574 | | 7/2009 |
| EP | 1 043 030 | A1 | 10/2000 |
| EP | 1 043 031 | A1 | 10/2000 |
| EP | 1 170 363 | A1 | 1/2002 |
| EP | 1 731 173 | A1 | 12/2006 |
| EP | 2 042 184 | A1 | 4/2009 |
| EP | 2 377 517 | A2 | 10/2011 |
| JP | 2-121932 | | 5/1990 |
| JP | 6-107565 | | 4/1994 |
| JP | 2000-302685 | | 10/2000 |
| JP | 2001-511171 | | 8/2001 |
| JP | 2001-286282 | | 10/2001 |
| JP | 2006-321763 | | 11/2006 |
| JP | 2007-99631 | | 4/2007 |
| JP | 2008-504827 | | 2/2008 |
| WO | WO 98/58630 | | 12/1998 |
| WO | WO 99/33489 | | 7/1999 |
| WO | WO 01/34115 | A2 | 5/2001 |
| WO | WO 2004/060059 | A2 | 7/2004 |
| WO | WO 2005/092389 | A1 | 10/2005 |
| WO | WO 2006/002538 | A1 | 1/2006 |
| WO | WO 2007/043486 | A1 | 4/2007 |
| WO | WO 2007/136134 | A1 | 11/2007 |
| WO | WO 2008/010341 | A1 | 1/2008 |

OTHER PUBLICATIONS

Li et al., Ann. NY Acad. Sciences, 2006, 1082, 1-8.*

Chinese Office action mailed Apr. 2, 2013 for corresponding Chinese Patent Application No. 201180009063.8 including English translation; 8pp.

Extended European Search Report for corresponding European Patent Application No. 11711242.5, dated Jan. 30, 2012, 6pp.

Takashima, et al., "Spray-drying preparation of microparticles containing cationic PLGA nanospheres as gene carriers for avoiding aggregation of nanospheres," International Journal of Pharmaceutics, vol. 343, 2007, pp. 262-269.

Tahara, et al., "Establishing chitosan coated PLGA nanosphere platform loaded with wide variety of nucleic acid by complexation with cationic compound for gene delivery," International Journal of Pharmaceutics, vol. 354, 2008, pp. 210-216.

Zou, et al., "Preparation and Characterization of Cationic PLA-PEG Nanoparticles for delivery of Plasmid DNA," Nanoscale Res Lett, vol. 4, 2009, pp. 982-992.

* cited by examiner

*Primary Examiner* — Kyle Purdy

(74) *Attorney, Agent, or Firm* — Christie, Parker & Hale, LLP

(57) ABSTRACT

The present invention provides a particulate pharmaceutical composition which has improved drug encapsulation stability and is suitable for a drug delivery system. The particulate pharmaceutical composition 1 contains: a plurality of block copolymer unit 2 arranged radially, each of which has a hydrophobic polymer-chain segment 2*b*, which is arranged radially inside, and a hydrophilic polymer-chain segment 2*a*, which is arranged radially outside; a drug 4, which includes a biomacromolecule; and a charged lipid 3, which has an electrical charge opposite to that of the drug 4; wherein the charged lipid 3 is being attracted to the hydrophobic polymer-chain segment 2*b*, and the drug 3 is positioned radially inside the hydrophobic polymer-chain segment 2*b*. The pharmaceutical composition 1 can effectively prevent the drug 4 from disengaging from the particle.

3 Claims, 3 Drawing Sheets

(a)

(b)

(a)

FREEZING OPERATION (b)

PARTICULATE PHARMACEUTICAL COMPOSITION

CROSS-REFERENCE TO RELATED APPLICATION

This application is a National Phase Patent Application and claims the priority of International Application No. PCT/JP2011/053052, filed on Feb. 14, 2011, which claims priority of Japanese Patent Application No. 2010-029486, filed on Feb. 12, 2010.

INCORPORATED BY REFERENCE

The material in the text file entitled "Y828.txt," amended Apr. 4, 2011 and being 1,880 bytes in size, is herein incorporated by reference in its entirety.

TECHNICAL FIELD

The present invention relates to a particulate pharmaceutical composition that can be used as a drug delivery system (DDS) and is constituted of a drug and a particulate carrier composition encapsulating the drug.

BACKGROUND ART

Biotechnology-based pharmaceuticals, which utilize biomacromolecules such as proteins and nucleic acids, are more susceptible to enzymatic degradation or immune elimination, compared with conventional pharmaceuticals based on low-molecular compounds. Patent Documents 1 to 3 disclose a DDS which contains a biomacromolecule within a liposome made of a lipid bilayer membrane, which intend to improve the in vivo stability of biotechnology-based pharmaceuticals.

PRIOR ART REFERENCES

Patent Documents

Patent Document 1: WO2001/034115
Patent Document 2: WO1998/58630
Patent Document 3: WO2005/092389

DISCLOSURE OF THE INVENTION

Problems to be Solved by the Invention

The conventional DDSs described in Patent Documents 1 to 3, in which the biomacromolecule drug is protected with a lipid bilayer membrane, are superior in in vivo stability of the drug, but are inferior in drug releasability from the carrier. In addition, due to the large particle size and also due to the electrical charge of the lipid which constitutes the lipid bilayer membrane, the conventional DDSs are likely to be captured by the reticuloendothelial system, such as the lungs, liver and spleen, and thereby removed from blood before reaching to the administration target.

A polymeric micelle formed with a block copolymer unit having a hydrophobic polymer-chain segment and a hydrophilic polymer-chain segment can be used as a DDS carrier, and the resultant DDS can be much smaller in particle size (e.g., the average particle size can be 100 nm or smaller) than the conventional DDSs using a liposome. However, such a DDS using a polymeric micelle as the carrier still has difficulty, in some cases, in delivering the drug to the administration target, due to lack of sufficient encapsulation force to maintain the biomacromolecule within the DDS particle as shown in the Comparative Examples, which will be explained later. In addition, such a DDS may sometimes cause the drug to disengage from the carrier during the storage period after production.

The present inventors have developed a polymeric micelle DDS. The outer surface of the micelle DDS is prevented from gathering a charged substance as a corollary of less electrical charge (Japanese Patent Application No. 2009-200681). This DDS is prevented from mis-delivering of drugs to the administration target as a corollary of less adhesion of a biomolecule onto the carrier surface. However, this DDS still has room to extend a duration of the drug encapsulation effect.

Means to Solve the Problems

The present invention provides a particulate pharmaceutical composition containing a block copolymer unit having a hydrophobic polymer-chain segment and a hydrophilic polymer-chain segment; a drug; and a charged lipid carrying a charge opposite to the charge of the drug. The drug includes at least a biomacromolecule selected from the group consisting of a protein and a nucleic acid. In the particulate pharmaceutical composition, a plurality of the block copolymer units are arranged radially with the hydrophobic polymer-chain segments radially inside and the hydrophilic polymer-chain segments radially outside. The charged lipid is being attracted to the hydrophobic polymer-chain segment. The drug is positioned radially inside the hydrophobic polymer-chain segments, whereby the drug is prevented from disengaging from the particle.

Effects of the Invention

The pharmaceutical composition according to the present invention has improved drug encapsulation stability and is suitable for DDS. This pharmaceutical composition can deliver the drug more reliably than the conventional DDSs, and is especially useful for an administration target that requires a longer period of drug delivering.

DESCRIPTION OF EMBODIMENTS

Figure 1:
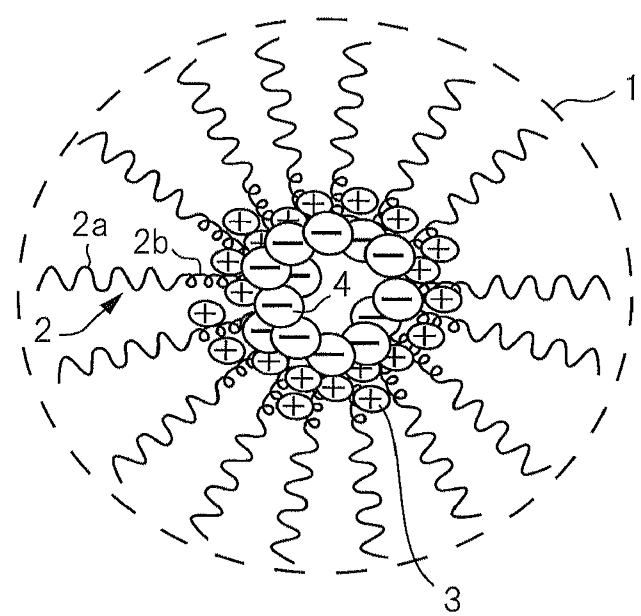
FIGS. 1(*a*) and 1(*b*) illustrate an example of the structure of the pharmaceutical composition of the present invention.
Figure 1:
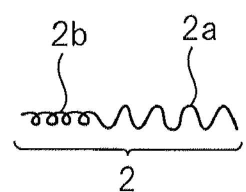
Figure 2:
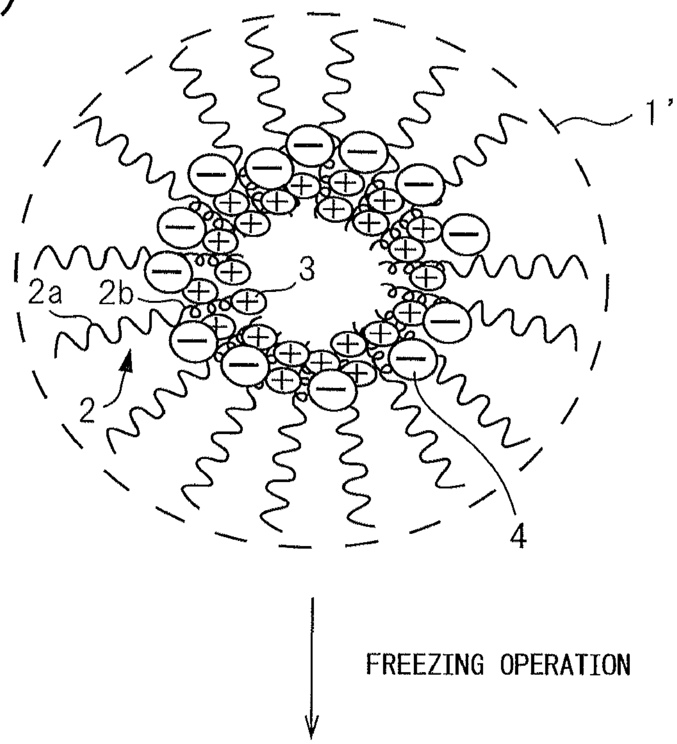
FIGS. 2(*a*) and 2(*b*) illustrate an example of drug distribution change in the particle between before and after freezing operation.
Figure 2:
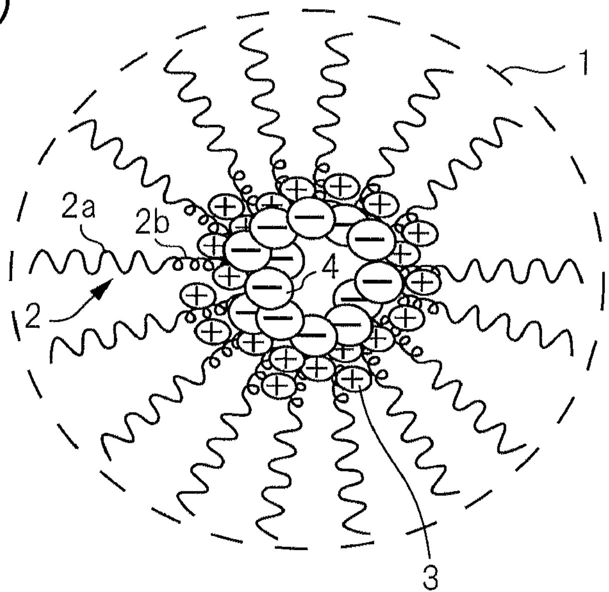

FIGS. 1 and 2 are referred to in the following description only for the purpose of helping the understanding of the present invention. FIGS. 1 and 2 are mere illustrative diagrams to which the present invention should not be limited. For example, although FIGS. 1 and 2 illustrate an example in which the charged lipid is cationic and the drug is anionic, the present invention should not be limited to this example.

FIG. 1 (*a*) illustrates an example of the structure of the particulate pharmaceutical composition according to the present invention (hereinafter also referred to as "pharmaceutical composition"). The pharmaceutical composition 1 contains a block copolymer unit 2, a charged lipid 3, and a drug 4. FIG. 1 (*b*) is an enlarged view of the block copolymer unit 2, which has a hydrophilic polymer-chain segment 2*a* and a hydrophobic polymer-chain segment 2*b*. The block copolymer units 2 are arranged radially in the pharmaceutical composition 1 with the hydrophobic polymer-chain segments 2*b* radially inside and the hydrophilic polymer-chain segments 2*a* radially outside. The charged lipid 3 carries a charge opposite to the charge of the drug 4, and is being attracted to the hydrophobic polymer-chain segments 2*b*.

In the pharmaceutical composition 1 according to the present invention, the drug 4 is positioned radially inside the hydrophobic polymer-chain segments 2*b*, as shown in FIG. 1 (*a*). This does not mean that all of the drugs 4 contained in the pharmaceutical composition 1 must be positioned radially inside the hydrophobic polymer-chain segments 2*b*; some of the drugs 4 may be positioned radially outside the hydrophobic polymer-chain segments 2*b*. This arrangement in the pharmaceutical composition 1 of the present invention serve to prevent the drugs 4 from disengaging from the particle, i.e., to improve encapsulation stability of the drugs 4.

The pharmaceutical composition 1 can be produced by, e.g., carrying out a freezing operation on a pharmaceutical composition precursor, in which the drug is positioned outside the hydrophobic polymer-chain segments 2*b*. The pharmaceutical composition precursor 1' can readily be formed by incorporating the drugs into a carrier composition in a known manner, as will be explained later. FIG. 2(*a*) illustrates distribution of the drugs 4 in the particle of the pharmaceutical composition precursor 1' before the freezing operation, and FIG. 2(*b*) illustrates distribution of the drugs 4 in the particle of the pharmaceutical composition precursor 1' after the freezing operation. As shown in FIG. 2(*a*), the drugs 4 are positioned outside the hydrophobic polymer-chain segments 2*b* in the particle of the pharmaceutical composition precursor 1'. Through the freezing operation, the drugs 4 move radially inward, resulting in the pharmaceutical composition 1 in which, as shown in FIG. 2(*b*), the drugs 4 are positioned radially inside the hydrophobic polymer-chain segments 2*b*. Thus, the pharmaceutical composition 1 of the present invention can be produced by transferring the drugs 4, which are positioned radially outside the hydrophobic polymer-chain segments 2*b* in the pharmaceutical composition precursor 1', to radially inside the hydrophobic polymer-chain segments 2*b* via the freezing operation. The reason why such drug transfer occurs is not exactly clear, but is believed that the arrangement of the block copolymers 2 and the charged lipids 3 forming the carrier composition is disturbed by the freezing operation to cause gaps, through which the drugs 4 are introduced into the inner part of the particle. The freezing operation may be carried out at least once, but should preferably be carried out twice or more. Repeating the freezing operation can facilitate introduction of the drugs 4 into the inner part of the particle.

The freezing operation may be any operation as long as it involves freezing of a certain composition, such as a freeze-drying operation and a freezing-and-thawing operation.

The freeze-drying (lyophilyzation) operation includes the steps of: freezing the composition (freezing step A); and drying the frozen composition (drying step). Freezing step A can be performed by maintaining the composition at a temperature of −200° C. or higher, preferably −100° C. or higher, and −10° C. or lower, preferably −20° C. or lower for a period of an hour or longer, preferably 5 hours or longer, and 72 hours or shorter, preferably 24 hours or shorter. Drying step can be performed by depressurizing the ambient pressure of the frozen composition to a vacuum state (e.g., 15 Pa or lower) to induce the water content to sublime. In order to facilitate sublimation, the ambient temperature should preferably be raised during depressurizing, either stepwise or continuously, to a temperature higher than the temperature at the freezing step, e.g., −20° C. or higher or −10° C. or higher. The upper limit for the raised ambient temperature may be about 25° C. The time duration of the drying step may be 5 hours or longer, preferably 20 hours or longer. The upper limit for the time length of the drying step may be, although not limited thereto, 100 hours. Since the pharmaceutical composition 1 obtained through the freeze-drying operation is in the dry state, it should preferably be dissolved into a known solvent, such as water when used.

Freezing-and-thawing operation includes the steps of: freezing the composition in a similar manner to the freezing step A; and thawing the frozen composition (thawing step). Thawing step can be performed by maintaining the composition at a temperature of 4° C. or higher, preferably 10° C. or higher, and 40° C. or lower, preferably 30° C. or lower for a period of 30 minutes or longer, preferably an hour or longer, and 24 hours or shorter, preferably 5 hours or shorter.

Whether the drugs 4 are positioned radially inside the hydrophobic polymer-chain segments 2*b* can be determined based on, e.g., whether the absolute value of the zeta potential of the pharmaceutical composition 1 is higher than that of a drug-containing particle which has the same constitution as the pharmaceutical composition 1 but is produced without freezing operation. This is because the drugs 4 move away from the outer surface of the particle toward the inner part of the particle through the freezing operation, whereby the charged lipids 3 increase its influence on the absolute value of the zeta potential of the pharmaceutical composition 1.

The charged lipid 3 herein means either an anionic lipid, which has more negative charges than positive charges in an aqueous medium with a physiological pH (e.g., pH7.4), or a cationic lipid, which has more positive charges than negative charges in the aqueous medium. Lipids which have both cationic and anionic groups (i.e., so-called amphoteric lipids) should also be judged based on the same criterion.

The charged lipid 3 retains the drug 4 within the pharmaceutical composition 1 via electrostatic bonding. The charged lipid 3 may only have an electrical charge opposite to the charge of the drug 4 at least in the storage environment of the pharmaceutical composition 1. The charged lipid 3 should preferably have a charge opposite to that of the drug 4 under physiological environments, such as in blood (e.g., pH7.4).

The charged lipids 3 are being attracted to the hydrophobic polymer-chain segments 2*b* by the following mechanism. The carrier composition, which is a base material for the pharmaceutical composition 1 of the present invention, can be formed by a method including, e.g., the step of suspending the block copolymer units 2 and the charged lipids 3 into an aqueous solution. The hydrophobic polymer-chain segments 2*b* of the block copolymer units 2 cannot disperse, but form an aggregate, in the aqueous solution due to their hydrophobicity, while the hydrophilic polymer-chain segments 2*a* can disperse, and move freely, in the aqueous solution. Thus, the block copolymer units 2 are arranged radially in the aqueous solution, with the hydrophobic polymer-chain segments 2*b* radially inside and the hydrophilic polymer-chain segments 2*a* radially outside. The charged lipids 3 are being attracted to the hydrophobic polymer-chain segments 2*b*, since they are highly hydrophobic and have higher affinity for the hydrophobic polymer-chain segments 2*b* than for water or the hydrophilic polymer-chain segments 2*a*. Thus, the charged lipids 3 are arranged away from the outer surface of the carrier composition and, even after the freezing operation explained below, are kept being attracted to the hydrophobic polymer-chain segments 2$b$.

In the pharmaceutical composition 1 of the present invention, the charged lipids 3 are being attracted to the hydrophobic polymer-chain segments 2$b$, whereby the outer surface of the pharmaceutical composition 1 is prevented from being charged so as to attract a substance which has a charge opposite to that of the charged lipids 3 (e.g., blood proteins). This state can be confirmed based on, i.e., whether the absolute value of the zeta potential of the pharmaceutical composition 1 is lower than a predetermined value. More specifically, the absolute value of the zeta potential of the pharmaceutical composition 1 should preferably be 15 mV or lower, more preferably 12 mV or lower, still more preferably 6 mV or lower, even more preferably 3 mV or lower. The zeta potential can be measured by adding the carrier composition or the pharmaceutical composition 1 to 10 mM HEPES buffer solution (pH 7.4) in such an amount as for the ratio of the total charged lipids to the buffer solution to be 0.1 mg/ml.

The ratio by weight of the amount of the block copolymer units to the amount of the charged lipids 3 should preferably be 1.0 or higher, more preferably 1.5 or higher, still more preferably 2.0 or higher, and preferably 50 or lower, more preferably 20 or lower, still more preferably 10 or lower. The higher the ratio, the lower the absolute value of the zeta potential of the pharmaceutical composition 1. On the other hand, drugs can be introduced more actively into the particle as the ratio of the charged lipids 3 becomes higher, for which reason the ratio should preferably be limited to 50 or lower as mentioned above.

The lipids may be a simple lipid, a conjugated lipid or a derived lipid. Examples thereof include phospholipids, glycoglycerolipids, glucosphingolipids, sphingoids and sterols. Specifically, examples of cationic lipids include 1,2-dioleoyl-3-trimethylammoniopropane (DOTAP), N-(2,3-dioleoyloxypropan-1-yl)-N,N,N-trimethylammonium chloride (DOTMA), 2,3-dioleoyloxy-N-[2-(sperminecarboxyamide) ethyl]-N,N-dimethyl-1-propanaminium trifluoroacetate (DOSPA), 1,2-dimyristyloxypropyl-3-dimethylhydroxyethylammonium bromide (DMRIE), 1,2-dioleoyloxypropyl-3-diethylhydroxyethylammonium bromide (DORIE), and 3β-[N—(N'N'-dimethylaminoethyl)carbamoyl]cholesterol (DC-Chol). Examples of anionic lipids include cardiolipin, diacylphosphatidylserine, diacylphosphatidic acid, N-succinyl phosphatidylethanolamine (N-succinyl PE), phosphatidic acid, phosphatidylinositol, phosphatidylglycerol, phosphatidylethylene glycol, and cholesterol succinate. The pharmaceutical composition 1 may contain two or more kinds of charged lipids 3.

The hydrophilic polymer-chain segment 2$a$ should preferably be a water-soluble polymer-chain segment made of polyethyleneglycol or polyoxyethylene. The molecular weight of the hydrophilic polymer-chain segment 2$a$ should preferably be 2,500 Da or higher, more preferably 5,000 Da or higher, still more preferably 8,000 Da or higher, and preferably 200,000 Da or lower, more preferably 20,000 Da or lower, still more preferably 15,000 Da or lower. The hydrophobic polymer-chain segment 2$b$ should preferably be a segment derived from a polyamino acid chain, part or all of which can form the α-helix in the pharmaceutical composition 1, whereby the charged lipids 3 can be attracted to the α-helix of the polyamino acid chain, i.e., dispersed around the α-helix. The number of repeating units in the hydrophobic polymer-chain segment 2$b$ should preferably be 10 or higher, more preferably 20 or higher, and preferably 200 or lower, more preferably 100 or lower, still more preferably 60 or lower. In order to reduce the absolute value of the zeta potential of the pharmaceutical composition 1, i.e., to reduce the surface charge of the pharmaceutical composition 1 (to be closer to neutral), the size of the hydrophilic polymer-chain segment 2$a$ (molecular weight) should preferably be larger than the size of the hydrophobic polymer-chain segment 2$b$ (the number of repeating units) in the block copolymer unit 2. The hydrophilic polymer-chain segment 2$a$ and/or the hydrophobic polymer-chain segment 2$b$ may form a branched structure. For example, a single chain of one segment may be coupled to two or more chains of the other segment.

The hydrophilic polymer-chain segment 2$a$ and the hydrophobic polymer-chain segment 2$b$ may also have a charged substituent such as an amino group and carboxy group, as long as the outer particle surface of the pharmaceutical composition 1 does not bear a charge which can attract a charged substance.

The hydrophilic polymer-chain segment 2$a$ and the hydrophobic polymer-chain segment 2$b$ can be linked to each other by covalently bonding the termini of their main chains. More specifically, examples of the block copolymer unit 2 are the compounds represented by general formulae (I) and (II). The pharmaceutical composition 1 may contain two or more kinds of the block copolymer units 2.

(I)

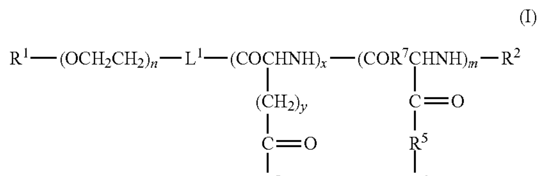

(II)

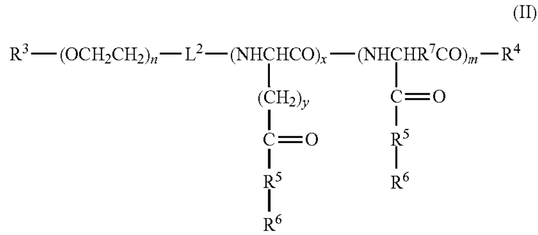

In formulae (I) and (II), $R^1$ and $R^3$, independently of each other, is either hydrogen atom or a group represented by $R^8(R^9)CH(CH_2)_q$— (where $R^8$ and $R^9$: i) independently of each other, is hydrogen atom, $C_{1-6}$ alkoxy group, aryloxy group, aryl-$C_{1-3}$-oxy group, cyano group, carboxy group, amino group, $C_{1-6}$-alkoxy carbonyl group, $C_{2-7}$-acylamide group, tri-$C_{1-6}$-alkyl siloxy group, siloxy group, or silylamino group; ii) together with each other, form ethylene dioxy group or propylene dioxy group, which are either unsubstituted or substituted with $C_{1-3}$-alkyl group; or iii) together with CH group to which they are bound, form formyl group);

q is an integer of from 0 to 10;

$R^2$ is hydrogen atom, saturated or unsaturated $C_1$-$C_{29}$ aliphatic carbonyl group, or arylcarbonyl group;

$R^4$ is hydroxy group, saturated or unsaturated $C_1$-$C_{30}$-aliphatic oxy group, or aryl-lower-alkyloxy group;

$R^5$ is —O— or —NH—;

$R^6$ is hydrogen atom, phenyl group, benzyl group, —$(CH_2)_4$-phenyl group, $C_4$-$C_{16}$ alkyl group which is either unsubstituted or substituted with amino group or carbonyl group, or sterol derivative residue;

$R^7$ is methylene group;

n is an integer of from 55 to 4,600;

x is an integer of from 10 to 200;

m is an integer of from 0 to 200 (wherein when m is one or more, the (COCHNH) units and the ($COR^7CHNH$) unit(s) can be arranged in any order, and when m is two or more, $R^6$ is selected for each amino acid unit independently of each other and can be arranged in the block copolymer in a random order, provided that hydrogen atoms must not account for 75% or more of $R^6$);

y is 1 or 2;

$L^1$ is a linking group selected from —NH—, —O—, —O—Z—NH—, —CO—, —$CH_2$—, and —O—Z—S—Z—NH— (where Z, independently of each other, means $C_1$-$C_6$ alkylene group); and $L^2$ is a linking group selected from —OCO—Z—CO—, and —NHCO—Z—CO— (wherein Z is $C_1$-$C_6$ alkylene group).

In formulae (I) and (II), n is an integer of preferably 110 or larger, more preferably 180 or larger, and preferably 460 or smaller, more preferably 340 or smaller;

x is an integer of preferably 20 or larger, and preferably 100 or smaller, more preferably 60 or smaller; and m is an integer of preferably 100 or smaller, more preferably 60 or smaller.

The block copolymer unit 2 may be an anionic polymer, a cationic polymer, or a neutral polymer. As used herein, polymers which have more negative charges than positive charges in an aqueous medium with a physiological pH (e.g., pH7.4) are regarded as anionic, polymers which have more positive charges than negative charges in the aqueous medium are regarded as cationic, and polymers which have substantially equal amounts of positive charges and negative charges in the aqueous medium are regarded as neutral.

The block copolymer unit 2 can be formed, e.g., by coupling a polymer having a hydrophilic polymer chain and a polymer having a polyamino acid chain in a know manner, optionally after purifying the polymers, if necessary, to restrict the molecular weight distribution. The block copolymer unit 2 according to formula (I) also can be formed, e.g., by the steps of: performing anion living polymerization using an initiator which can add $R^1$ to form a polyethyleneglycol chain; introducing an amino group to the growing end; and polymerizing, at the amino end, an N-carboxy anhydride (NCA) of a protected amino acid, such as N$\epsilon$-Z-L-lysin, β-benzyl-L-aspartate, or γ-benzyl-L-glutamate.

The carrier composition can be formed, e.g., as follows. First, a block copolymer unit and a charged lipid, optionally together with a neutral lipid, are fully dissolved or dispersed into a forming solution containing an organic solvent, after which the organic solvent is removed by evaporation. Examples of organic solvents include acetone, dichloromethane, dimethylformamide, dimethylsulfoxide, acetonitrile, tetrahydrofuran, and methanol. The forming solution may contain two or more organic solvents, and also may contain a small amount of water. The resultant solid or paste is combined with water or an aqueous solution containing an additive such as an appropriate salt or stabilizer, followed by stirring to disperse the block copolymer unit and the lipid(s). The resultant product is further dispersed/pulverized by means of, e.g., ultrasonic irradiation, high-pressure emulsification or extruder to thereby form the carrier composition.

The drug 4 is retained in the pharmaceutical composition 1 via electrostatic bonding with the charged lipid 3. Thus, the link between the charged lipid 3 and the drug 4 is reversible, and does not involve any chemical structural change. The drug 4 can be introduced into the carrier composition either by adding the drug 4 to the forming solution in the production of the carrier composition, or by adding the carrier composition to a solution of the drug 4.

Examples of the drug 4 include: anionic compounds, which have more negative charges than positive charges in an aqueous medium with a physiological pH (e.g., pH7.4); and cationic compounds, which have more positive charges than negative charges in the aqueous medium. The compounds should preferably be macromolecular compounds.

The drug 4 should preferably be a biomacromolecule. The biomacromolecule herein means a macromolecule of biological origin or a structural analogue thereto, and more specifically, should preferably be at least one selected from a protein and a nucleic acid. There are no limitations to the alternatives and sizes of proteins and nucleic acids, and the proteins include peptides. Such a biomacromolecule is at least partially hydrophilic; especially, nucleic acids exhibit very high hydrophilicity.

Accordingly, even if preparing a composite of a biomacromolecule (e.g., a nucleic acid) and a lipid charged oppositely to the biomacromolecule, and trying to introduce the composite into a conventional polymer micelle particle which does not contain a charged lipid, it would be difficult to transfer the composite to inside the polymer micelle particle by mean of hydrophobic interaction. This is because the biomacromolecule having a polar portion would surround the charged lipid and render the composite surface nearly hydrophilic (i.e., much less hydrophobic than at least than the hydrophobic portion of the block copolymer existing near the polymer micelle surface).

In order to prevent the drug 4 either from disengaging from the pharmaceutical composition 1 in blood too early or from being encapsulated in the pharmaceutical composition 1 for too long a time, the charge ratio between the charged lipid 3 and the drug 4 in the pharmaceutical composition 1 should preferably be controlled to be within a particular range. When the drug 4 is, e.g., a nucleic acid, the charge ratio can be defined as [the mol concentration of cationic groups of the charged lipid contained in the pharmaceutical composition]/[the mol concentration of phosphoric groups in the nucleic acid]. On the other hand, when the drug 4 is a compound which has both anionic and cationic groups, e.g., a protein, the charge ratio can be defined as [the mol concentration of cationic groups of the charged lipid contained in the pharmaceutical composition]/([the mol concentration of groups in the drug which are charged oppositely to the charged lipid]—[the mol concentration of groups in the drug which are charged similarly to the charged lipid]). The charge ratio should preferably be 0.5 or higher, more preferably one or higher, still more preferably 2 or higher, and preferably 50 or lower, more preferably 20 or lower, still more preferably 10 or lower.

The average particle sizes of the carrier composition and the pharmaceutical composition 1 should preferably be 10 nm or larger, more preferably 30 nm or larger, and preferably 300 nm or smaller, more preferably 200 nm or smaller.

EXAMPLES

The present invention will be explained in more detail below by referring to Examples.

I. Preparation of Particulate Pharmaceutical Compositions:

Particulate pharmaceutical compositions were prepared in accordance with the following procedure, and subjected to the measurements explained below.

I-1. Preparation of Particulate Carrier Compositions:

I-1-1. Preparation of Particulate Carrier Composition a (with PEG-PBLG):

Five grams of α-methoxy-ω-amino-polyethyleneglycol (hereinafter also referred to as "PEG") having a weight-average molecular weight (Mw) of 10000 (Manufactured by NOF Corp.) was dissolved into 50 ml of dimethyl sulfoxide, which was reacted with 5.5 g (42 parts with respect to polyethyleneglycol) of N-carboxy anhydride (NCA) of γ-benzyl-L-glutamate (hereinafter also referred to as "PBLG") at 40° C. for 24 hours. The reaction solution was dropped into 1 L of a mixture solvent of hexane and ethyl acetate (volume ratio 1:1) to cause precipitation of a polymer, which was recovered by filtration under reduced pressure and then dried to yield 8.6 g of a solid product. This product was dissolved into 86 ml of DMF, with which 432 μl of acetic anhydride was mixed and reacted at 40° C. for 24 hours. The reaction solution was dropped into 1 L of a mixture solvent of hexane and ethyl acetate (volume ratio 1:1) to cause precipitation of a polymer, which was recovered by filtration under reduced pressure and then further dried to yield 8.1 g of polyethyleneglycol-poly (γ-benzyl-L-glutamate)-Ac block copolymer (hereinafter also referred to as "PEG-PBLG"), which is a neutral polymer. The structural formula of PEG-PBLG is shown below. $^1$H-NMR analysis revealed that the degree of polymerization of the PBLG block was 40.

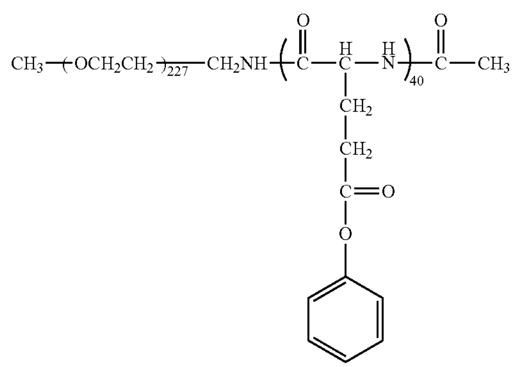

The resultant PEG-PBLG(10-40) (block copolymer unit) was mixed with DOTAP (cationic lipid) and DOPE (neutral lipid) at the ratios of 2.5/1/1 by weight in chloroform, and dried under reduced pressure until solid was obtained. This mixture was combined with 10 mM HEPES buffer (pH7.4), stirred at 4° C. overnight, pulverized by ultrasonic irradiation, and passed through a 0.22 μm filter to thereby yield a solution of lipid micelle containing PEG-PBLG (hereinafter also referred to as "particulate carrier composition A").

I-1-2. Preparation of Particulate Carrier Composition B (with PEG-pGlu(Bn)):

PEG-PBLG was alkali-treated to deprotect the benzyl groups of the glutamic acid side chains, whereby polyethyleneglycol/poly(L-glutamic acid) block copolymer was obtained (hereinafter also referred to as "PEG-pGlu"). The glutamic acid side chains of PEG-pGlu were partially modified with benzyl groups ($PhCH_2$) via condensation reaction using benzyl alcohol to thereby yield polyethyleneglycol/benzyl-introduced poly(L-glutamic acid) block copolymer (hereinafter also referred to as "PEG-pGlu(Bn)"), which is an anionic polymer. $^1$H-NMR analysis revealed that the number of benzyl groups introduced was 35 per polymer. The structural formula of PEG-pGlu(Bn) is shown below.

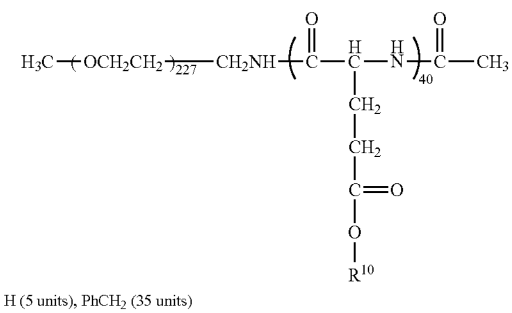

$R^{10}$: H (5 units), $PhCH_2$ (35 units)

One milliliter of an acetone solution (50 mg/mL) of the resultant PEG-pGlu(Bn) (block copolymer unit) was mixed with 0.5 mL of a methanol solution (40 mg/mL) of DOTAP (cationic charged lipid) and 0.5 mL of a methanol solution (40 mg/mL) of DOPE (neutral lipid), and dried under reduced pressure until solid was obtained. The resultant mixture was combined with 2.5 mL of 100 mM sodium phosphate buffer (pH7.4), stirred for three hours at room temperature, pulverized by ultrasonic irradiation (130 W, 1 second pulse, 10 minutes), and passed through a 0.22 μm filter (Millex GP, Millipore) to thereby yield a solution of lipid micelle containing PEG-pGlu(Bn) (hereinafter also referred to as "particulate carrier composition B").

I-2. Preparation of Pharmaceutical Compositions Via Freezing Operation:

I-2-1. Preparation of Pharmaceutical Compositions Using Freezing-and-Thawing Operation:

SiRNA was dissolved into 10 mM HEPES buffer (pH7.4) to prepare 40 μl siRNA solution, which was mixed with the lipid micelle solution containing PEG-PBLG as a block copolymer unit (particulate carrier composition A), 10 mM HEPES buffer and 50% sucrose solution to prepare a solution of lipid micelle containing, as a drug, siRNA shown in each Example (hereinafter also referred to as "particulate pharmaceutical composition A"). The concentrations of siRNA and sucrose in the particulate pharmaceutical composition solution were adjusted to 10 μM and 10%, respectively. The mixture ratio between the cationic lipid (DOTAP) and the siRNA was also adjusted so as for the charge ratio (+/−) of the concentration of positive charges (cationic group) of the cationic lipid (DOTAP) to the concentration of negative charges (phosphoric group) of siRNA to be 8.

In each of the Examples described in the present description, siRNA was selected from the ones explained below, all of which are available from Nippon EGT Co., Ltd.

siRNA(Luc): Designed to target the firefly luciferase gene, this siRNA is composed of a sense strand of 5'-CUUACGCUGAGUACUUCGAdTdT-3' (SEQ ID NO:1) and an antisense strand of 5'-UCGAAGUACUCAGCGUAAGdTdT-3' (SEQ ID NO:2) double-stranded in a conventional manner.

siRNA(Plk1): Designed to target the human Plk1 (Polo-like kinase 1) gene, this siRNA is composed of a sense strand of 5'-CCAUUAACGAGCUGCUUAAdTdT-3'

(SEQ ID NO:3) and an antisense strand of 5'-UUAAG-CAGCUCGUUAAUGGdTdT-3' (SEQ ID NO:4) double-stranded in a conventional manner. The Plk1 gene is a kinase which plays a role in the M phase of cell division. SiRNA(Plk1) induces apoptosis when introduced into the cell.

F-siRNA(Luc): This siRNA is formed in the same manner as siRNA(Luc) except that the antisense strand of SEQ ID NO:2 is Cy3-labeled at the 5' end (5'-Cy3-UC-GAAGUACUCAGCGUAAGdTdT-3').

The resultant solution of siRNA-encapsulated lipid micelle (particulate pharmaceutical composition A) was subjected to the measurements explained below, either without any other treatment or after receiving freezing-and-thawing operation once, twice, or thrice. Each freezing-and-thawing operation was carried out by freezing the composition at −80° C. for 12 hours, and thawing it at room temperature for an hour.

Hereinafter, the untreated particulate pharmaceutical composition A is also referred to as "the pharmaceutical composition of Reference Example 1," the particulate pharmaceutical composition A which received the freezing-and-thawing operation once is also referred to as "the pharmaceutical composition of Example 1," the particulate pharmaceutical composition A which received the freezing-and-thawing operation twice is also referred to as "the pharmaceutical composition of Example 2," and the particulate pharmaceutical composition A which received the freezing-and-thawing operation thrice is also referred to as "the pharmaceutical composition of Example 3." In addition, each of the pharmaceutical compositions of Reference Example 1 and Examples 1 to 3, as well as the pharmaceutical compositions of Reference Example 2 and Example 4 explained below, is also referred to simply as "sample" without distinction.

In each of the pharmaceutical compositions of Reference Example 1 and Examples 1 to 3, the charged lipid (DOTAP) retains the drug (siRNA) in the particle via electrostatic bonding while being attracted to the hydrophobic polymer-chain segment, whereby the outer particle surface is prevented from bearing a charge which can attract a substance charged oppositely to the charged lipid. In addition, in each of the pharmaceutical compositions of Reference Example 1 and Examples 1 to 3, the hydrophobic polymer-chain segment derived from a polyamino acid chain (PBLG) is believed to form the α-helix, around which the charged lipid (DOTAP) is dispersed. Further, in each of the pharmaceutical compositions of Examples 1 to 3, the drug is positioned inside the hydrophobic polymer-chain segment.

I-2-2. Preparation of the Pharmaceutical Composition Using Freeze-Drying Operation:

To 100 μM siRNA aqueous solution, a solution of lipid micelle containing PEG-pGlu(Bn) as the block copolymer unit (particulate carrier composition B) and sucrose were mixed, and let stand still at 4° C. for two hours to prepare a solution of lipid micelle containing, as a drug, siRNA shown in each Example (hereinafter also referred to as "particulate pharmaceutical composition B"). The concentrations of siRNA and sucrose in the particulate pharmaceutical composition solution were adjusted to 20 μM and 10%, respectively. The mixture ratio between the cationic lipid (DOTAP) and the siRNA was also adjusted so as for the charge ratio (+/−) of the concentration of positive charges (cationic group) of the cationic lipid (DOTAP) to the concentration of negative charges (phosphoric group) of siRNA to be 8.

The resultant solution of siRNA-encapsulated lipid micelle (particulate pharmaceutical composition B) was subjected to the measurements explained below, either without any other treatment or after it was received freeze-drying operation in a conventional manner to form a stock, and then dissolved into water again. The freeze-drying operation was carried out using Triomaster II A-04 (manufactured by NISSEI Ltd.).

Hereinafter, the untreated particulate pharmaceutical composition B is also referred to as "the pharmaceutical composition of Reference Example 2," and the particulate pharmaceutical composition B which received the freeze-drying operation is also referred to as "the pharmaceutical composition of Example 4."

In each of the pharmaceutical compositions of Reference Example 2 and Example 4, the charged lipid (DOTAP) retains the drug (siRNA) in the particle via electrostatic bonding while being attracted to the hydrophobic polymer-chain segment, whereby the outer surface of the particulate composition is prevented from gathering a charged substance, which has an opposite charge of the charged lipid, as a corollary of less electrical charge. In addition, in each of the pharmaceutical compositions of Reference Example 2 and Example 4, the hydrophobic polymer-chain segment derived from a polyamino acid chain (pGlu(Bn)) is believed to form the α-helix, around which the charged lipid (DOTAP) is dispersed. Further, in the pharmaceutical composition of Example 4, the drug is positioned radially inside the hydrophobic polymer-chain segment.

II. Measurements of Particulate Pharmaceutical Compositions:

II-1. Light-Scattering Measurement:

This measurement was carried out using, as a sample, each of the pharmaceutical compositions of Reference Example 1 (untreated), Example 1 (freezing-and-thawing once), Example 2 (freezing-and-thawing twice) and Example 3 (freezing-and-thawing thrice), which were prepared in accordance with the procedure described in "I. Preparation of particulate pharmaceutical compositions" using siRNA(Luc) as the siRNA and PEG-PBLG (neutral polymer) as the block copolymer unit, as well as Reference Example 2 (untreated) and Example 4 (freeze-drying), which were prepared likewise but using PEG-pGlu(Bn) (cationic polymer) as the block copolymer unit.

Each sample was diluted with 10 mM HEPES buffer so as for the siRNA concentration to be 1 μM. The micelles in each sample were measured for particle size, scattering intensity, and the absolute value of the zeta potential with the light-scattering analyzer (Zetasizer Nano ZS, Malvern Instruments).

The results of measurement for particle size and zeta potential are shown in Table 1.

Comparison of the pharmaceutical compositions of Examples 1 to 3 with the pharmaceutical composition of Reference Example 1, each of which was prepared using PEG-PBLG (neutral polymer) as the block copolymer unit, shows that in each of the pharmaceutical compositions of Example 1 (freezing-and-thawing once), Example 2 (freezing-and-thawing twice) and Example 3 (freezing-and-thawing thrice), there were no significant changes in the particle size and the scattering intensity of the micelles, but there was an increase in the absolute value of the zeta potential, compared to the pharmaceutical composition of Reference Example 1 (untreated). Taking into consideration the fact that the particle size and the scattering intensity did not change substantially, the increase in zeta potential is believed to be due to relative increase in the positive charge at the micelle surface caused by transfer of siRNA into the inner part of the micelle, not due to dissociation of the lipid from the micelle.

TABLE 1

| Pharmaceutical composition | Particle size (nm) | Absolute value of zeta potential (mV) |
|---|---|---|
| Reference Example 1 (PEG-PBLG, untreated) | 116 | 6.85 |
| Example 1 (PEG-PBLG, freezing/thawing × 1) | 120 | 9.00 |
| Example 2 (PEG-PBLG, freezing/thawing × 2) | 122 | 11.10 |
| Example 3 (PEG-PBLG, freezing/thawing × 3) | 122 | 11.10 |
| Reference Example 2 (PEG-pGlu(Bn), untreated) | 147 | 0.455 |
| Example 4 (PEG-pGlu(Bn), freeze-drying) | 190 | 0.421 |

II-2. Measurement of Encapsulation Rate:

This measurement was carried out using, as a sample, each of the pharmaceutical compositions of Reference Example 1 (untreated), Example 1 (freezing-and-thawing once), Example 2 (freezing-and-thawing twice) and Example 3 (freezing-and-thawing thrice), which were prepared in accordance with the procedure described in "I. Preparation of particulate pharmaceutical compositions" using siRNA(Luc) as the siRNA and PEG-PBLG (neutral polymer) as the block copolymer unit, as well as Reference Example 2 (untreated) and Example 4 (freeze-drying), which were prepared likewise but using PEG-pGlu(Bn) (cationic polymer) as the block copolymer unit.

II-2-1. Preparation of Calibration Curve:

A series of diluted reference solutions, each of which has a volume of 50 μL, was prepared by diluting 40 μM siRNA solution with 10 mM HEPES buffer serially by one third (resulting in 11 reference solutions ranging from 40 μM to 0.68 nM). Each reference solution of 50 μL from the resultant series was measured for fluorescence intensity to prepare a calibration curve in accordance with the following procedure. 50 μL of each reference solution was mixed with 750 μL of 10 mM HEPES buffer and 200 μL of 1% TRITONX-100 aqueous solution. 100 μL from the resultant mixture solution was put into each well of a 96-well plate (black). After adding 100 μL of PicoGreen™ solution (diluted by 1/200 with 10 mM HEPES buffer) to each well followed by mixing, the mixture was left standing at room temperature in the absence of light for five minutes, and measured for fluorescence intensity using a plate reader to plot a calibration curve. Since the resultant calibration curve was linear within the siRNA concentration range of from 1.48 μM to 2 nM, the samples were measured within this range.

II-2-2. Measurement of Samples:

Each sample was diluted (standardized) with 10 mM HEPES buffer (pH7.4) so as for the siRNA concentration to be 1 μM. 500 μL of the solution was ultracentrifuged (100,000×g, 4° C., an hour) to sediment the micelles, and 50 μL of the supernatant was collected stilly. The collected supernatant was measured for fluorescence intensity in accordance with the procedure explained in "II-2-1. Preparation of calibration curve," and the obtained fluorescence intensity was collated with the calibration curve to determine the standardized non-encapsulated siRNA concentration, which is the concentration of siRNA in the supernatant derived from each sample. The siRNA encapsulation rate of the micelles in each sample was determined in accordance with the following equation:

$$\text{SiRNA encapsulation rate (\%)}=(1-x)\times 100$$

where x means the standardized non-encapsulated siRNA concentration (μM).

II-2-3. Results:

The resultant siRNA encapsulation rates are shown in Table 2. In each of the pharmaceutical compositions of Reference Examples 1 and 2 and Examples 1 to 4, the supernatant after ultracentrifuging contained very little siRNA, and almost all of the siRNA was included in the micelles.

TABLE 2

| Pharmaceutical composition | Encapsulation rate (%) |
|---|---|
| Reference Example 1 (PEG-PBLG, untreated) | 99.1 |
| Example 1 (PEG-PBLG, freezing/thawing × 1) | 99.5 |
| Example 2 (PEG-PBLG, freezing/thawing × 2) | 99.5 |
| Example 3 (PEG-PBLG, freezing/thawing × 3) | 99.4 |
| Reference Example 2 (PEG-pGlu(Bn), untreated) | 96.6 |
| Example 4 (PEG-pGlu(Bn), freeze-drying) | 98.3 |

II-3. Evaluation of Encapsulation Stability:

This measurement was carried out using, as a sample, each of the pharmaceutical compositions of Reference Example 1 (untreated) and Example 3 (freezing-and-thawing thrice), which were prepared in accordance with the procedure described in "I. Preparation of particulate pharmaceutical compositions" using siRNA(Luc) as the siRNA and PEG-PBLG (neutral polymer) as the block copolymer unit, as well as Reference Example 2 (untreated) and Example 4 (freeze-drying), which were prepared likewise but using PEG-pGlu (Bn) (cationic polymer) as the block copolymer unit.

Dextran sulfate, an anionic macromolecular, was added to each sample, and the ratio of the siRNA replaced with dextran sulfate and released from the micelles (siRNA release rate) was measured to evaluate the encapsulation stability of each sample. More specifically, the evaluation was carried out as follows. Each sample was mixed with an excess dextran sulfate (the charge ratio of which to siRNA is 80), and diluted with 10 mM HEPES buffer (pH7.4) so as for the siRNA concentration to be 1 μM (i.e., standardized). 500 μL of the obtained solution was ultracentrifuged (100,000×g, 4° C., one hour) to sediment the micelles, and 50 μL of the supernatant was collected stilly. The collected supernatant was measured for fluorescence intensity in accordance with the procedure explained in "II-2-1. Preparation of calibration curve," and the obtained fluorescence intensity was collated with the calibration curve obtained in "II-2-2. Measurement of samples" to determine the standardized non-encapsulated siRNA concentration in the supernatant derived from each sample, which indicates the amount of the siRNA released from the micelles in each sample. The siRNA release rate (the ratio of the amount of siRNA replaced with dextran sulfate and released from the micelles to the amount of siRNA originally included in the micelle) was determined in accordance with the following equation:

$$\text{siRNA release rate (\%)}=\{(y-x)/1\}\{y-x\}\times 100$$

where x means the standardized non-encapsulated siRNA concentration (μM); and y means the amount of siRNA released from the micelles (μM).

Figure 3:
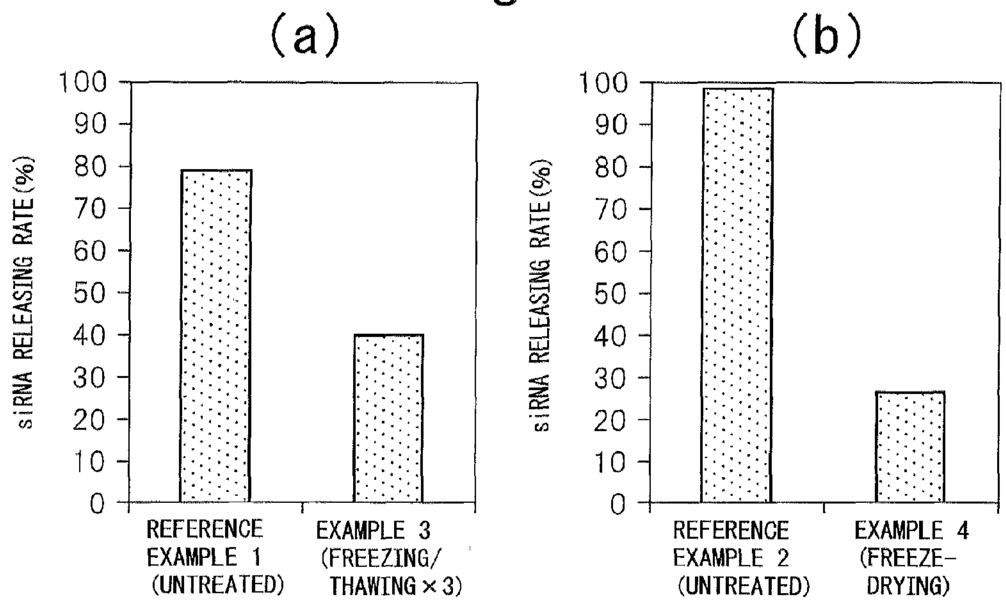
FIGS. 3(*a*) and 3(*b*) indicate evaluation results of drug encapsulation stability of pharmaceutical compositions.

The results are shown in FIG. 3. Comparison of the pharmaceutical compositions of Example 3 and Reference Example 1, both of which were prepared using PEG-PBLG (neutral polymer) as the block copolymer unit, shows that the pharmaceutical composition of Example 3, which was obtained through freezing operation, had a reduced siRNA release rate, which is about half that of the pharmaceutical composition of Reference Example 1, which received no freezing operation. Comparison of the pharmaceutical compositions of Example 4 and Reference Example 2, both of which were prepared using PEG-pGlu(Bn) (cationic polymer) as the block copolymer unit, also shows that the pharmaceutical composition of Example 4, which was obtained through freezing operation, had a reduced siRNA release rate which is about 30% as that of the pharmaceutical composition of Reference Example 2.

II-4. Evaluation of Remaining Rate in Blood:

This measurement was carried out using, as a sample, each of the pharmaceutical compositions of Reference Example 1 (untreated) and Example 3 (freezing-and-thawing thrice), which were prepared in accordance with the procedure described in "I. Preparation of particulate pharmaceutical compositions" using F-siRNA(Luc) as the siRNA and PEG-PBLG (neutral polymer) as the block copolymer unit, as well as Reference Example 2 (untreated) and Example 4 (freeze-drying), which were prepared likewise but using PEG-pGlu (Bn) (cationic polymer) as the block copolymer unit.

Each sample was administered to Balb/c mice (obtained from Charles River Laboratories Japan, Inc.) via the tail vein, and 200 μl of blood was collected via the inferior vena cava one hour after. The dosage of each sample for each mouse was determined so as for the ratio of F-siRNA to the weight of the mouse to be 1 mg/kg. The collected blood was centrifuged with 2000×g at 4° C. for 10 minutes, and 80 μl of plasma was collected from the supernatant. The plasma was measured for fluorescence intensity using a plate reader (POWERSCAN HT, manufactured by Dainippon Sumitomo Pharma Co., Ltd.) (excitation wavelength: 485 nm; fluorescence wavelength: 528 nm) to determine the quantity of F-siRNA circulating in blood, as an indicator of remaining rate in blood.

Figure 4:
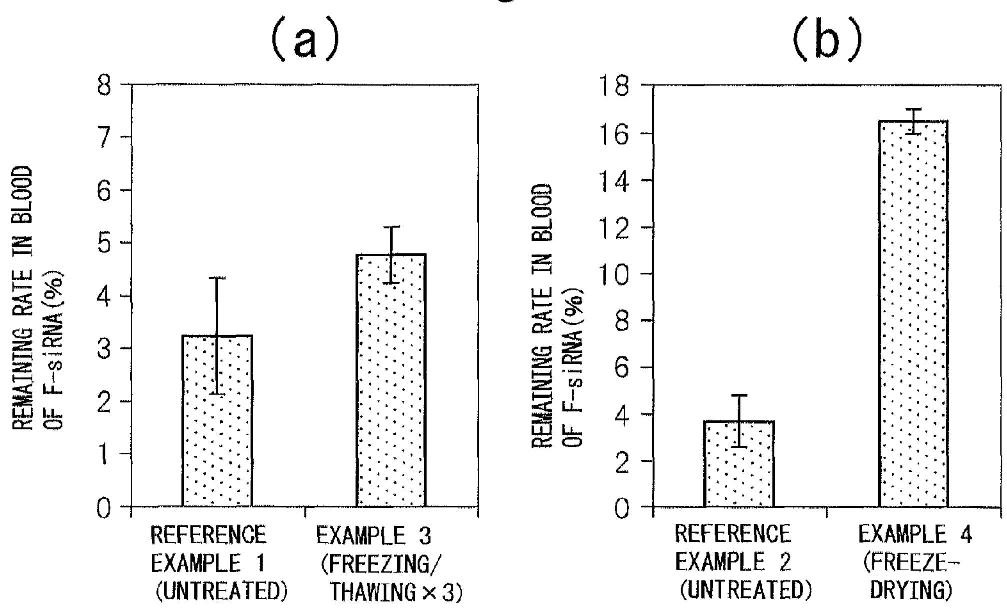
FIGS. 4(*a*) and 4(*b*) indicate evaluation results of blood circulation of pharmaceutical compositions.

The results are shown in FIG. 4. Comparison of the pharmaceutical compositions of Example 3 and Reference Example 1, both of which were prepared using PEG-PBLG (neutral polymer) as the block copolymer unit, shows that the pharmaceutical composition of Example 3, which was obtained through freezing operation, resulted in more F-siRNA remaining in blood, i.e., higher remaining rate in blood. Comparison of the pharmaceutical compositions of Example 4 and Reference Example 2, both of which were prepared using PEG-pGlu(Bn) (cationic polymer) as the block copolymer unit, also shows that the pharmaceutical composition of Example 4, which was obtained through freezing operation, resulted in more F-siRNA remaining in blood, higher remaining rate in blood.

The invention claimed is:

1. A particulate pharmaceutical composition comprising:

a plurality of block copolymer units, each unit having a hydrophobic polymer-chain segment and a hydrophilic polymer-chain segment, the hydrophobic polymer-chain segment being a polyamino acid segment, the plurality of block copolymer units being arranged radially with the hydrophobic polymer-chain segments radially inside and the hydrophilic polymer-chain segments radially outside;

a plurality of charged lipids carrying a first charge, the plurality of charged lipids being attracted to the hydrophobic polymer-chain segment; and a drug carrying a second charge opposite to the first charge and comprising a biomacromolecule selected from the group consisting of proteins and nucleic acids, wherein the particulate pharmaceutical composition is subjected to freezing, wherein the drug is positioned radially inside relative to the hydrophobic polymer-chain segments as a result of the freezing such that the drug is prevented from disengaging from the particulate pharmaceutical composition, and wherein the particulate pharmaceutical composition has an absolute zeta potential that is higher than that of a particulate pharmaceutical composition that has not been subjected to the freezing.

2. The particulate pharmaceutical composition according to claim 1, wherein part or all of the polyamino acid chain forms an α-helix.

3. The particulate pharmaceutical composition according to claim 2, wherein the charged lipid is dispersed around the α-helix.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial
<220> FEATURE:
<223> OTHER INFORMATION: a sense strand of a double-strand siRNA
      designed to target firefly luciferase gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 1

cuuacgcuga guacuucgan n                                          21


<210> SEQ ID NO 2
<211> LENGTH: 21
<212> TYPE: RNA
<213> ORGANISM: Artificial
<220> FEATURE:
<223> OTHER INFORMATION: an antisense strand of a double-strand siRNA
      designed to target firefly luciferase gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 2

ucgaaguacu cagcguaagn n                                          21


<210> SEQ ID NO 3
```

```
<211> LENGTH: 21
<212> TYPE: RNA
<213> ORGANISM: Artificial
<220> FEATURE:
<223> OTHER INFORMATION: a sense strand of a double-strand siRNA
      designed to target Human Polo-like kinase 1 gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 3

ccauuaacga gcugcuuaan n                                        21


<210> SEQ ID NO 4
<211> LENGTH: 21
<212> TYPE: RNA
<213> ORGANISM: Artificial
<220> FEATURE:
<223> OTHER INFORMATION: an antisense strand of a double-strand siRNA
      designed to target Human Polo-like kinase 1 gene
<220> FEATURE:
<221> NAME/KEY: misc_feature
<222> LOCATION: (20)..(20)
<223> OTHER INFORMATION: n stands for deoxythymidine
<220> FEATURE:
<221> NAME/KEY: misc_feature
<222> LOCATION: (21)..(21)
<223> OTHER INFORMATION: n stands for deoxythymidine

<400> SEQUENCE: 4

uuaagcagcu cguuaauggn n                                        21
```